(12) United States Patent
Ashraf et al.

(10) Patent No.: US 9,096,731 B2
(45) Date of Patent: *Aug. 4, 2015

(54) POLYMERIC FILM EXHIBITING IMPROVED ANTI-BLOCKING CHARACTERISTICS AND PROCESS OF MAKING

(71) Applicant: The Proctor & Gamble Company, Cincinnati, OH (US)

(72) Inventors: Arman Ashraf, Mason, OH (US); Daniel Steven Wheeler, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 383 days.

This patent is subject to a terminal disclaimer.

(21) Appl. No.: 13/628,553

(22) Filed: Sep. 27, 2012

(65) Prior Publication Data

US 2013/0030399 A1 Jan. 31, 2013

Related U.S. Application Data

(63) Continuation of application No. 11/413,545, filed on Apr. 28, 2006, now Pat. No. 8,304,599.

(60) Provisional application No. 60/676,275, filed on Apr. 29, 2005.

(51) Int. Cl.
| | | |
|---|---|---|
| A61F 13/15 | (2006.01) |
| A61F 13/20 | (2006.01) |
| A61F 13/49 | (2006.01) |
| B29C 33/58 | (2006.01) |
| C08J 7/04 | (2006.01) |
| A61F 13/494 | (2006.01) |
| A61F 13/514 | (2006.01) |

(Continued)

(52) U.S. Cl.
CPC ........... *C08J 7/047* (2013.01); *A61F 13/15203* (2013.01); *A61F 13/49413* (2013.01); *A61F 13/51405* (2013.01); *B29C 37/0067* (2013.01); *C08J 7/065* (2013.01); *B29C 33/58* (2013.01); *B29C 33/60* (2013.01); *B29C 33/62* (2013.01); *B29C 33/64* (2013.01); *B29C 33/66* (2013.01); *B29C 37/0071* (2013.01); *B29L 2007/00* (2013.01); *C08J 2491/00* (2013.01); *Y10T 156/10* (2015.01)

(58) Field of Classification Search
None
See application file for complete search history.

(56) References Cited

U.S. PATENT DOCUMENTS

| | | |
|---|---|---|
| 2,088,844 A | 8/1937 | De Alzugaray |
| 3,088,844 A | 5/1963 | Hungerford et al. |

(Continued)

FOREIGN PATENT DOCUMENTS

| | | |
|---|---|---|
| EP | 0408197 * | 1/1991 |
| EP | 696 502 B1 | 2/2001 |

(Continued)

OTHER PUBLICATIONS

PCT Search Report, mailed May 12, 2006 (15 pages).

*Primary Examiner* — Jeffrey Wollschlager
(74) *Attorney, Agent, or Firm* — William E. Gallagher

(57) ABSTRACT

A method of forming a film resistant to blocking including the steps of providing a polymeric film having a first and second surface; applying the anti-blocking agent in a fluid or molten state to at least the first surface of the polymeric film; and gathering the treated film. The anti-blocking agent may be substantially acrylic free.

10 Claims, 10 Drawing Sheets

(51) Int. Cl.
*C08J 7/06* (2006.01)
*B29C 33/60* (2006.01)
*B29C 37/00* (2006.01)
*B29C 33/66* (2006.01)
*B29C 33/62* (2006.01)
*B29C 33/64* (2006.01)
*B29L 7/00* (2006.01)

(56) References Cited

U.S. PATENT DOCUMENTS

| | | | |
|---|---|---|---|
| 3,297,476 A | 1/1967 | Kane | |
| 3,462,290 A * | 8/1969 | Alix et al. | 427/365 |
| 3,505,842 A | 4/1970 | Taylor | |
| 3,751,281 A * | 8/1973 | Peterson et al. | 427/172 |
| 3,848,594 A | 11/1974 | Buell | |
| 3,860,003 A | 1/1975 | Buell | |
| 4,100,324 A | 7/1978 | Anderson et al. | |
| 4,121,006 A | 10/1978 | Harada et al. | |
| 4,233,352 A * | 11/1980 | Ono et al. | 428/141 |
| 4,309,469 A | 1/1982 | Varona | |
| 4,476,180 A * | 10/1984 | Wnuk | 428/220 |
| 4,489,117 A * | 12/1984 | Ono et al. | 428/147 |
| 4,515,595 A | 5/1985 | Kievit et al. | |
| 4,695,278 A | 9/1987 | Lawson | |
| 4,699,622 A | 10/1987 | Toussant et al. | |
| 4,699,845 A | 10/1987 | Oikawa et al. | |
| 4,795,454 A | 1/1989 | Dragoo | |
| 4,894,060 A | 1/1990 | Nestegard | |
| 4,946,527 A | 8/1990 | Battrell | |
| 5,102,734 A * | 4/1992 | Marbrow et al. | 428/349 |
| 5,130,189 A * | 7/1992 | Hart | 428/331 |
| 5,151,092 A | 9/1992 | Buell et al. | |
| 5,156,793 A | 10/1992 | Buell et al. | |
| 5,167,897 A | 12/1992 | Weber et al. | |
| 5,221,274 A | 6/1993 | Buell et al. | |
| 5,242,436 A | 9/1993 | Weil et al. | |
| 5,554,145 A | 9/1996 | Roe et al. | |
| 5,569,234 A | 10/1996 | Buell et al. | |
| 5,571,096 A | 11/1996 | Dobrin et al. | |
| 5,571,586 A | 11/1996 | Gobran | |
| 5,580,411 A | 12/1996 | Nease et al. | |
| 5,629,063 A | 5/1997 | Gobran | |
| 5,723,087 A | 3/1998 | Chappell et al. | |
| 5,733,628 A | 3/1998 | Pelkie | |
| 5,994,453 A * | 11/1999 | Banning et al. | 524/590 |
| 6,004,306 A | 12/1999 | Robles et al. | |
| 6,057,024 A | 5/2000 | Mleziva et al. | |
| 6,426,390 B1 | 7/2002 | Hahnfeld et al. | |
| 6,432,098 B1 | 8/2002 | Kline et al. | |
| 6,437,014 B1 | 8/2002 | Ho et al. | |
| 6,777,082 B2 | 8/2004 | Patel et al. | |
| 6,803,014 B2 | 10/2004 | Ho et al. | |
| 6,815,475 B2 | 11/2004 | Donald et al. | |
| 6,914,091 B2 | 7/2005 | Donald et al. | |
| 7,524,984 B2 | 4/2009 | Smith et al. | |
| 7,603,317 B2 | 10/2009 | Adler et al. | |
| 7,943,813 B2 | 5/2011 | Petryk et al. | |
| 8,158,849 B2 * | 4/2012 | Ashraf et al. | 604/370 |
| 8,304,599 B2 * | 11/2012 | Ashraf et al. | 604/370 |
| 2001/0048991 A1 | 12/2001 | Martin et al. | |
| 2002/0061981 A1 | 5/2002 | Donald et al. | |
| 2002/0061982 A1 | 5/2002 | Donald et al. | |
| 2003/0021925 A1 * | 1/2003 | Schmal et al. | 428/35.7 |
| 2004/0067284 A1 * | 4/2004 | Sankey et al. | 426/106 |
| 2004/0127872 A1 * | 7/2004 | Petryk et al. | 604/382 |
| 2005/0079372 A1 * | 4/2005 | Schmal et al. | 428/482 |
| 2006/0055089 A1 | 3/2006 | Zhang et al. | |

FOREIGN PATENT DOCUMENTS

GB 361790 A 11/1932
GB 695555 A 9/1953

* cited by examiner

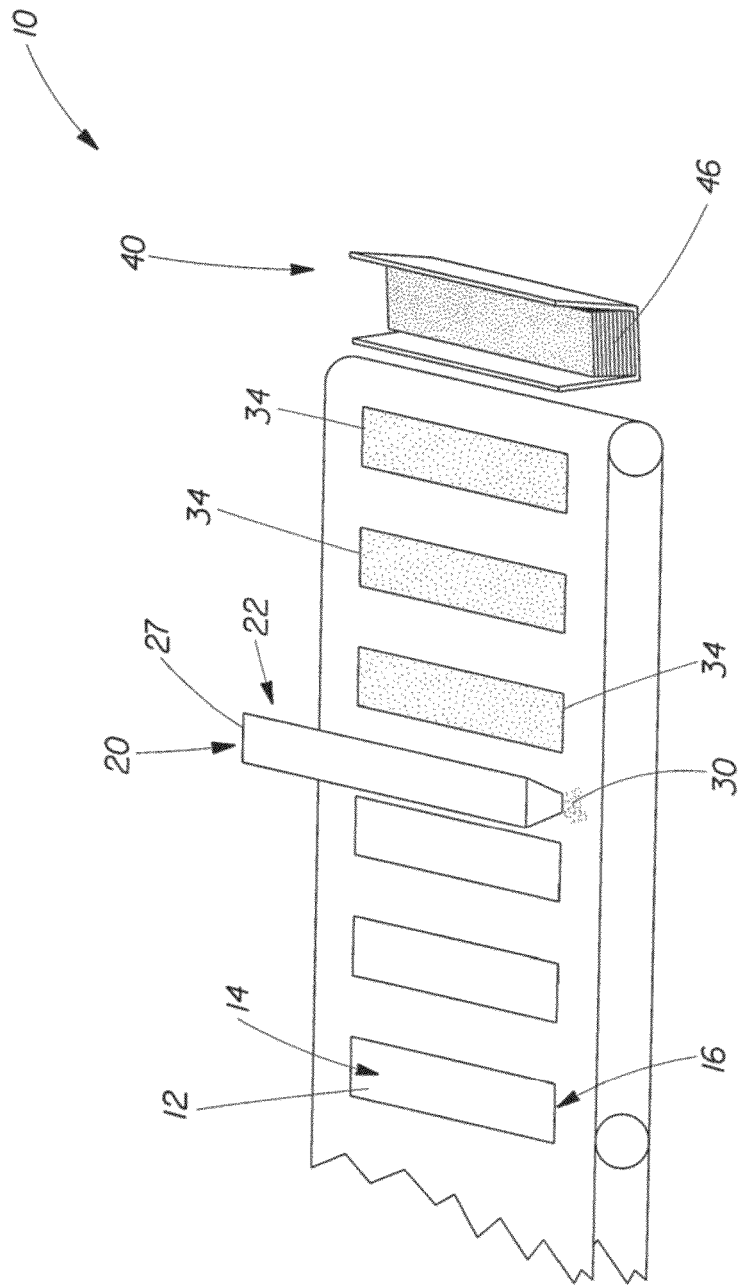

POLYMERIC FILM EXHIBITING IMPROVED ANTI-BLOCKING CHARACTERISTICS AND PROCESS OF MAKING

This application is a continuation of U.S. Nonprovisional Application Ser. No. 11/413,545, filed Apr. 28, 2006 (now U.S. Pat. No. 8,304,599), which claims the benefit of U.S. Provisional Application Ser. No. 60/676,275, filed Apr. 29, 2005, the entirety of which is incorporated by reference herein.

FIELD OF THE INVENTION

The present invention relates generally to a method for improving the anti-blocking characteristics of a polymeric film, the resulting polymeric film, and consumer goods comprising, the polymeric film.

BACKGROUND OF THE INVENTION

Polymeric films are commonly used in a variety of commercial and consumer goods. In particular, polymeric films have been used in disposable consumer goods such as disposable absorbent articles including diapers, catamenial products, and adult incontinence devices. These films are readily processable and can be used to improve exudate containment of the absorbent article. Furthermore, elastomeric films, which are polymer films exhibiting elastic properties, are commonly used in absorbent articles. Elastomeric films allow the absorbent article to provide a snug fit that can accommodate a range of different sized wearers and to provide a gasketing-seal to the wearer's skin. Elastomeric films are often combined with other materials such as nonwoven materials to form stretch laminates that may be used in absorbent articles.

Most polymeric films are supplied such that they need to be resized, laminated, or otherwise processed prior to incorporation into a consumer good. Generally, polymeric films are supplied in a bulk form such as a hulk roll or other configuration where multiple layers of the film are in face-to-face contact. However, one drawback of polymeric films provided as such is that the film tends to block or adhere together, blocking can be permanent such that the force to separate the film layers exceeds the tensile strength of the film. Permanent blocking is seen where the film tears before the individual film layers separate, in some cases, the blocking may be reversible. The blocked films may be separated with an elevated unwind tension. However, the unwound film may have imperfections that are remnants of the blocking. Blocking may be further exacerbated by storage at elevated temperature or pressure. Both conditions are common for storage of films supplied in bulk rolls.

Bulk, rolls are often formed by winding the film onto a spool at some take-up tension that is imparted to the film. The outer concentric film layers apply a pressure to the inner layers. The bulk roll may remain in this configuration for several days, weeks, or months while being stored and/or shipped. The severity of blocking is also a function of the film's composition. Blocking is seen more frequently in a relatively soft film of polyvinyl chloride) as opposed to a relatively hard film of high density polyethylene.

A variety of strategies have been used to reduce or eliminate the blocking effect in films. One strategy to reduce blocking involves compounding anti-blocking agents directly into the film composition. Generally, anti-blocking agents may be added into the polymer and blended to achieve thorough mixing. Often the mixing will occur at an elevated temperature so that the polymer and anti-blocking agent are molten or able to flow. Common anti-blocking agents include natural and synthetic silica, talc and other minerals, and organic compounds. One drawback with the compounding of anti-blocking agents is the potential for diminished properties such as tensile strength. For elastomeric films, anti-blocking agents can negatively affect the force profile of the film.

Another strategy to reduce blocking involves applying an anti-blocking agent directly onto a cast polymer film. Anti-blocking agents such as silicas (natural and synthetic), talc, and other minerals are commonly applied to the surface of films in a solid powder or particulate form. However, powder application to a film being conveyed at commercial speeds can result in a dusting problem. The dust can create an industrial hygiene and safety hazard for personnel working in proximity to the process. The powder may also contaminate the process line and downstream components. From a performance perspective, particulate anti-blocking agents may have poor abrasion resistance. The powder is held to the surface, of the polymer film by the degree of tack exhibited by the film. Since the films may exhibit more cohesive than adhesive character (i.e., the film adheres to itself but not to other, dissimilar materials), the powder may be adhered loosely to the film. The powder may be removed from the surface of the film by abrasion or oscillation experienced in the process line. As a result, the powder treated film may still exhibit blocking.

Another strategy to reduce blocking involves the formation of as skin-layer on the polymer film. The skin layer may act as as physical barrier preventing self-contact of the polymer prone to blocking. It is known, especially for elastomeric films, that a polymer film prone to blocking can be coextruded with a thin skin layer of a polymer that is more resistant to blocking. As an alternative to an extruded skin, a low basis weight material, such as a nonwoven, may be used. The material is generally laminated to the film by some bonding means such as by use of an adhesive. Both types of skin layers have drawbacks. Given the large surface area over which a bulk roiled film may block, the skin layer generally is continuous over at least one surface of the film. As a result, a significant amount of material (e.g., anti-blocking polymer or nonwoven material) is needed to prevent the blocking of the film. Skin application requires additional process steps and complexity. Ultimately, the additional material and processing results in increased manufacturing cost.

In response to the above identified problems, it would be desirable to develop a method for combining an anti-blocking agent and a polymer film prone to blocking that does not require a coextruded or laminated skin layer, compounding of an anti-blocking agent, or powder application of an anti-blocking agent. Further, it would be desirable for the anti-blocking agent not to adversely affect the performance of the polymer film. It would also be desirable for the method to be applicable to both elastomeric and non-elastomeric films.

SUMMARY OF THE INVENTION

In order to solve the problems of the prior art, the present invention provides as method of forming a film resistant to blocking including the steps of providing a polymeric film having a first surface and a second surface, applying the anti-blocking agent in a fluid or molten state to at least the first surface of the polymeric film, and gathering the treated film. The anti-blocking agent may be substantially acrylic free.

The present invention may also provide a treated film comprising a polymeric film having a first and second surface and an anti-blocking agent disposed on at least the first surface of the polymeric film. The treated film may exhibit an average T-Peel force of less than or equal to 20 N/cm as measured by a T-Peel Test. The anti-blocking agent may be substantially acrylic free.

The present invention may also provide a diaper having a front waist region, as rear waist region, and a crotch region positioned between the front and rear waist regions. The diaper includes a liquid previous topsheet, a backsheet at least partially joined to the topsheet, an absorbent core positioned between the topsheet and backsheet. The diaper also may include an element such as a pair of side panels, a pair of leg cuffs, a waist feature, a fastening system, or combinations thereof. The element includes a treated film. The treated film includes a polymeric film having a first surface and a second surface and as formation disposed on at least the first surface of the polymeric film, said formation comprising anti-blocking agent. The anti-blocking agent may be substantially acrylic free. The treated film may exhibit an average T-Peel force of less than or equal to 20 N/cm as measured by a T-Peel Test.

BRIEF DESCRIPTION OF THE DRAWINGS

FIG. 2a is a perspective view of one embodiment of the process of the present invention.

DETAILED DESCRIPTION OF THE INVENTION

Figure 1:
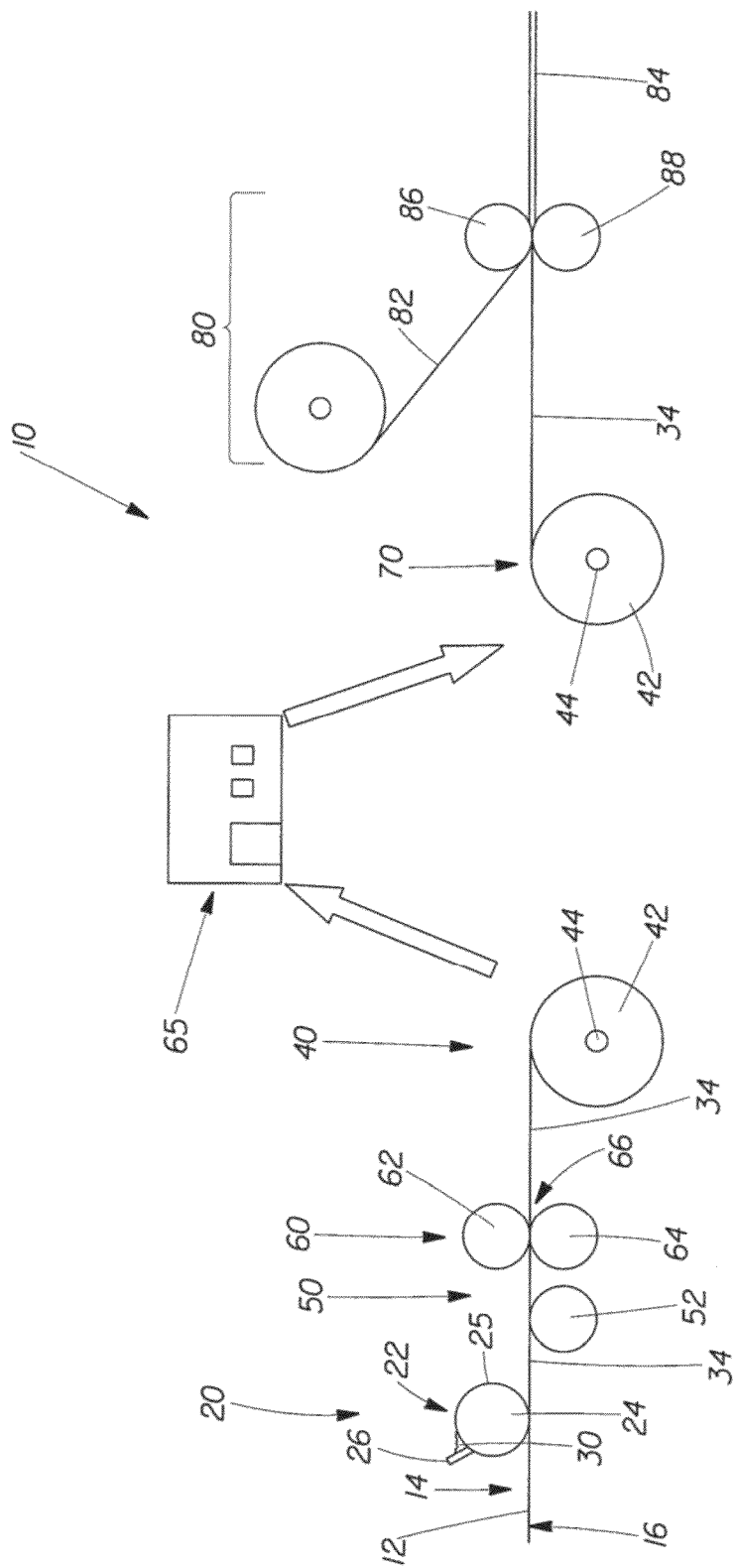
FIG. 1 is a schematic representation of one embodiment of the process of the present invention.

As used herein, the term "coating" refers to a substantially continuous layer of material (e.g., an anti-blocking agent) on a substrate (e.g., a polymeric film). Generally, a coating covers at least 90% of the surface area for a given surface of the substrate.

As used herein the term "extensible" refers to materials which elongate or increase in at least One dimension when subject to an external pulling force.

As used herein the terms "stretchable" or "elastic" are intended to be interchangeable and refer to materials which are extensible and which also return to substantially their original dimensions when the external pulling force is removed. It will be appreciated that the terms stretchable and elastic include the term extensible as each term is used herein.

As used herein the term "scale" refers to the three dimensional shape of a formation of material (e.g., an anti-blocking agent) on as substrate (e.g., as polymeric film). A scale is as substantially planar structure with a caliper generally smaller in dimension than the length or width of the scale as measured along, the planar face. However, portions of the scale may extend out of plane. The planar face may of the scale be irregularly shaped.

As used herein the term "gathered" refers to a material configured such that at least a first portion of the material is in face-to-face contact with a second portion of the material. The first portion, and the second portion may be areas on a same surface of the material. The first portion and the second portion may be areas on separate surfaces of the material. The first portion and second portion may be areas on discrete pieces of the material. The first portion and the second portion may be contiguous or incontiguous. The to "gathering" refers to placing the material in a "gathered" configuration.

As used herein the term "diaper" refers to an absorbent article generally won by infants or incontinent persons about the lower torso. The term "diaper" may encompass other similar absorbent articles worn about the lower torso including pull-on diapers or pant-type garments, training pants, incontinence briefs, incontinence undergarments, absorbent inserts, diaper holders and liners, feminine hygiene garments, and the like.

As used herein the term "blocking" refers to the self-adhesive character that certain polymer films may exhibit. Furthermore, in this invention, the term "blocking" is defined by reference the T-Peel Test, as described below. In the T-Peel test, a film is considered "blocked" if de-lamination occurs between an interface other than the interface between the two treated films (e.g., items 612a and 612b in FIG. 6d). If a specimen is "blocked" no values are to be reported for the peak and average force.

Every range given throughout this specification will include every narrower range that falls within such broader range as if such narrower ranges were all expressly written herein.

The present invention relates to a process for forming a blocking-resistant film. As will be appreciated from the description below, the blocking-resistant film may be formed with a variety of process steps and apparatus. The process generally includes the steps of providing a polymeric film, applying an anti-blocking agent to the polymeric film, and gathering the treated film. Other process steps are clearly within the realm of the present invention and certain exemplary steps are provided herein. While the steps may be performed in the order presented, it should be recognized that this disclosure is not so limited to the order in which the steps are presented but instead includes any order or any number of steps resulting in the claimed polymeric film with an anti-blocking agent disposed thereon.

Figure 2B:
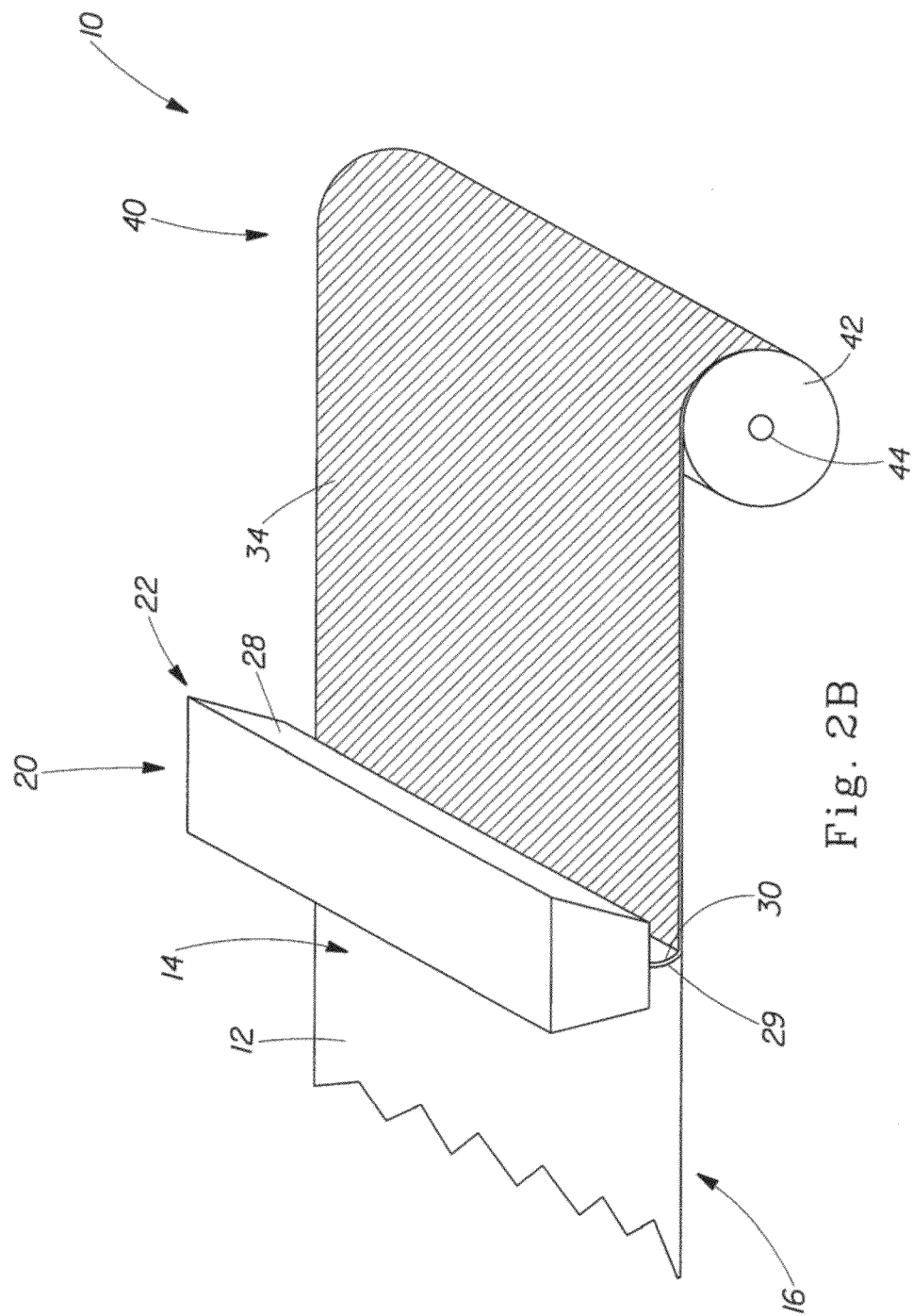
FIG. 2b is a perspective view of an alternative embodiment of the process of the present invention.

FIG. 1 shows one embodiment of a process 10 of the present invention with several optional process steps. FIGS. 2a and 2b show perspective views of other suitable process embodiments. The processes shown in FIGS. 1 and 2a-b each have the steps of providing a polymeric film 12, providing an anti-blocking agent 30 at an application station 20 to form a treated film 34, and gathering the treated film 34 at a gathering station 40.

A polymeric film 12 is provided having a first surface 14 and a second surface 16. The film 12 may be provided in a substantially continuous manner where the film is supplied continuously during, the normal operation of the process. The film 12 may be conveyed by any film conveyance mechanisms. In some embodiments, the film 12 may be provided by on-line formation. In such an embodiment, the process 10 may be equipped with an optional film funning station from which the film 12 may be provided. Suitable methods for forming polymeric films, including as variety of extrusion processes, are considered well known in the art. In other embodiments, the film 12 may be supplied from any storage or up-take device known in the art such as festooning, rolls or take-up rolls. Since a polymeric film may exhibit blocking when in contact with itself, any storage device may desirably be configured to prevent the film from adhering to itself. This may be done by maintaining the physical separation of the film or, if the film is in contact with itself, minimizing time, temperature, or pressure at which the film is in contact with itself.

In certain embodiments, such as illustrated in FIG. 2a, the polymeric film 12 may be provided and processed in a discontinuous manner where the film 12 is supplied as one or more discrete pieces. For example, the polymeric film 12 may be provided as a discrete panel so that the process is performed in a piecemeal or intermittent manner. Further processing steps described herein may be relevant to films supplied in a continuous or a discontinuous manner.

The polymeric film 12 may be any thermoplastic polymer known in the art. In certain embodiments, the polymeric film 12 comprises an elastomeric polymer. Suitable elastomeric polymers include thermoplastic elastomers that may be in the form of homopolymers and copolymers including but is not limited to block copolymers, random copolymers, alternating copolymers, and graft copolymers. The polymeric film 12 may comprise from about 0.01% to about 100%, by weight, of the thermoplastic elastomer. Suitable thermoplastic elastomers may include polyvinylarenes, polyolefins, metallocene-catalyzed polyolefins, polyesters, polyurethanes, polyether amides, and combinations thereof. Suitable polymeric films 12 may include vinylarene block copolymers. Block copolymers include variants such as diblock, triblock, tetrablock, or other multi-block copolymers having at least one vinylarene block. Exemplary vinylarene block copolymers include styrene-butadiene-styrene, styrene-isoprene-styrene, styrene-ethylene/butylene-styrene, styrene-ethylene/propylene-styrene, and the like. Commercially available styrenic block copolymers include KRATON® from the Kraton Polymer Corporation, Houston, Tex.; SEPTON® from Kuraray America, Inc., New York, N.Y.; and VECTOR® from Dexco Chemical Company, Houston, Tex. Commercially available metallocene-catalyzed polyolefins include EXXPOL®, EXACT®, and Vistanuxx® from Exxon Chemical. Company, Baytown, Tex.; AFFINITY® and ENGAGE® from Dow Chemical Company, Midland, Mich. Commercially available polyurethanes include ESTANTE® from Noveon, Inc., Cleveland, Ohio. Commercial available polyether amides include PEBAX® from Atofina Chemicals, Philadelphia, Pa. Commercially available polyesters include HYTREL® from E. I. DuPont do Nemours Co., Wilmington, Del. The polymeric film 12 may also contain various additives including viscosity modifiers, processing aids, colorants, fillers, stabilizers, anti-oxidants, and/or bacteriostats. These additives are well known in the art and may account for about 0.01% to about 60% of the total weight of the polymeric film. In certain embodiments, the composition comprises from about 0.01% to about 2.5% by weight or, alternatively, from about 0.01% to about 10% by weight of additives.

The polymeric film 12 may be conveyed to an application station 20. The application station 20 is responsible for the application of the anti-blocking agent 30 to the polymeric film 12 to form a treated film 34. The station 20 may include an applicator device 22. The applicator 22 may store, process, mix, heat, and/or dispense the anti blocking agent 30.

The anti-blocking agent 30 may be applied in a molten, fluid, or solid state to the polymeric film 12. In certain embodiments, the applicator 22 may be heated so that the agent 30 is able to flow and be conveyed and delivered by the applicator 22. However, a heating element may be employed apart from the applicator 22. Upon deposit of the molten or softened anti-blocking agent 30 onto the polymeric film 12, the anti-blocking agent 30 may act as a thermal mass thereby warming the polymeric film 12 in proximity to the deposited agent 30. The polymeric film 12 may be warmed to its softening or melting point. Interaction of the molten or softened anti-blocking agent 30 with the molten or softened polymeric film 12 can result in fusion of the film 12 and agent 30 upon cooling and solidification. This fusion may be beneficial to produce a treated film 34 wherein the anti-blocking agent 30 thereon is resistant to abrasion and rub-off.

In some cases, the polymeric film 12 may exhibit an adhesive or selective adhesive character. In such cases, the anti-blocking agent 30 may be held to the polymeric film 12 by the adhesive or selective adhesive property of the film 12.

In certain embodiments, the polymeric film 12 is provided in a continuous manner by on-line formation such as by extrusion through a die. The step of applying the anti-blocking agent 30 may be performed concurrently with the formation of the film 12 (e.g., anti-blocking agent 30 is applied to the polymeric film 12 as it exits an extruder die) or at some point after formation of the film 12. Application of the anti-blocking agent 30 concurrent or substantially concurrent to the formation of the film 12 may provide for better adhesion of the agent 30 to the film 12. It is believed that if the film 12 is at or slightly below its melting or softening temperature when the molten or soften agent 30 is applied, then the film 12 and agent 30 are prone to increased molecular diffusion. This may result in increased adhesion of the anti-blocking agent 30 to the polymeric film 12.

Suitable applicators 22 may be capable of metering the amount of anti-blocking agent 30 applied to the polymeric film 12. The applicator 22, may meter an amount of anti-blocking agent 30 to provide a treated film 34 with some prescribed basis weight (i.e., some mass of agent 30 per area of polymeric film 12). In suitable embodiments, the applicator 22 may apply the anti-blocking agent 30 so as to result in a basis weight of no more than about 20 g/m$^2$. Alternatively, the applicator 22 may apply the anti-blocking agent 30 so as to result in a basis weight of no more than about 15 g/m$^2$, 10 g/m$^2$, 7.5 g/m$^2$, 5.0 g/m$^2$, or 2.5 g/m$^2$. However, the applicator 22 may apply the agent 30 so as to result in basis weights in excess of 20 g/m$^2$.

In certain embodiments, the anti-blocking agent 30 may be applied in a quantity enabling formation of a coating upon deposit and spread of the molten anti-blocking agent 30 onto the polymeric film 12. In other embodiments, it may be desirable to reduce the amount of anti-blocking agent 30 applied to the polymeric film 12. In such cases, it may be desirable that the applicator 22 apply the anti-blocking agent 30 onto the polymeric film 12 in a manner that prevents the formation of a coating. For example, the anti-blocking agent 30 may be applied such that it does not cover more than 90% of the surface area of polymeric film 12 to which the anti-blocking agent 30 is applied. In other embodiments, the anti-blocking agent 30 may cover less than 75% of the surface area of the polymeric film 12; alternatively, less than 60% of the surface area of the polymeric film 12; alternatively, less than 50% of the surface area of the polymeric film 12; alternatively, less than 40% of the surface are of the polymeric film 12; alternatively, less than 30% of the surface are of the polymeric film 12; alternatively, less than 20% of the surface are of the polymeric, film 12; alternatively, less than 10% of the surface are of the polymeric film 12; or alternatively, less than 5% of the surface are of the polymeric film 12.

A variety of applicators 22 may be used in the present inventions to deliver the anti-blocking agent 30 to the polymeric film 12. Gravure rolls, reverse rolls, knife-over folk, metering rods, slot extruders, immersion baths, curtain coaters, spray applicators (including pneumatic sprayers, airless sprayers, air-assisted airless sprayers, and high-volume/low-pressure sprayers), extruders, co-extruders, and air knife coaters are examples of suitable applicators.

FIG. 1 shows the applicator 22 having a roll 24 with an exterior surface 25. The anti-blocking agent 30 may be applied to the exterior surface 25 of the roll 24. The roll 24 rotates and transfers at least a portion of the anti-blocking agent 30 to the film 12. A doctor blade 26 may be used to meter the amount of anti-blocking agent 30 that roll 24 transfers to the film 12.

FIG. 2a depicts the applicator 22 as a sprayer 27. The anti-blocking agent 30 is dispensed as a fine mist from the sprayer 27 and disposed on the polymeric film 12. Conventional spray applicators may use a stream of pressurized gas, typically air, to atomize a fluid or molten stream of the anti-blocking agent 30. Another suitable spray applicator is an airless spray applicator, instead of using a pressurized, gas to atomize the anti-blocking agent 30, hydraulic pressure may be applied to the anti-blocking agent 30. Other spray applicator variants suitable for use include air-assisted airless spraying and high-volume/low-pressure spraying.

FIG. 2b depicts the applicator 22 as a slot coater 28. The slot water 28 dispenses a stream 29 of anti-blocking agent 30 in a continuous or discontinuous manner onto the polymeric, film 12.

In certain embodiments, the applicator 22 may be capable of atomizing the anti-blocking, agent 30. In certain embodiments, the applicator 22, may be capable of atomizing, the agent 30 to produce a mist with an average particle size of no greater than about 1000 μm. Alternatively, the average particle size may be no greater than about 750 μm, 500 μm, 250 μm, or 100 μm.

The anti-bloc-king agent 30 may be applied to the first surface 14 of the polymeric film 12 as shown in FIGS. 1 and 2a-b. In certain embodiments, the anti-blocking agent 30 may alternatively be applied to the second surface 16 of the polymeric film 12.

The applicator 22 may be able to apply the anti-blocking agent 30 in a manner so as to result in a variety of formations on the polymeric film 12. FIGS. 3a-f shows various anti-blocking agent 30 formations that may result from application of the agent 30 onto the film 12. Suitable formations include, but are not limited to, discrete droplets (FIG. 3a), continuous and discontinuous stripes or bands (FIG. 3b), a substantially continuous layer (shown in a cut-away view in FIG. 3c), discrete scales that may be spaced (FIG. 3d), discrete scales that may be tightly packed or in contact (FIG. 3e), and continuous or discontinuous webs (FIG. 3f).

In certain embodiments, the anti-blocking agent 30 may form discrete droplets on the polymeric film 12. While not limited in shape, the droplets generally form a three-dimensional shape that is substantially or partially spherical, substantially or partially hemispherical, or that is bounded by a relatively planar face and a relatively rounded face. The droplets may partially coalesce or may be in contact with each other. Some droplets may form an agglomerate structure. The agglomerate structure may be discrete or may continuously coat the film 12. Generally the individual droplets that form the agglomerate structure will maintain a discernable three-dimensional shape. The droplets may have an approximate particle diameter of less than about 1000 μm. Alternatively, the droplet may have an approximate particle diameter of less than about 750 μm, 500 μm, 250 μm, or 100 μm.

Figure 4A:
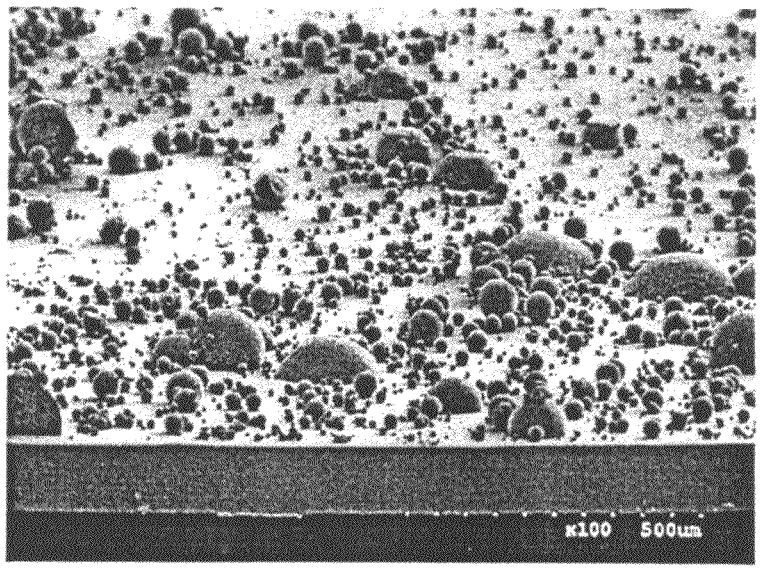
FIGS. 4a-f are scanning electron micrographs (acquired at 100× magnification) of a variety of anti-blocking agent formations on a polymeric film.
Figure 4B:
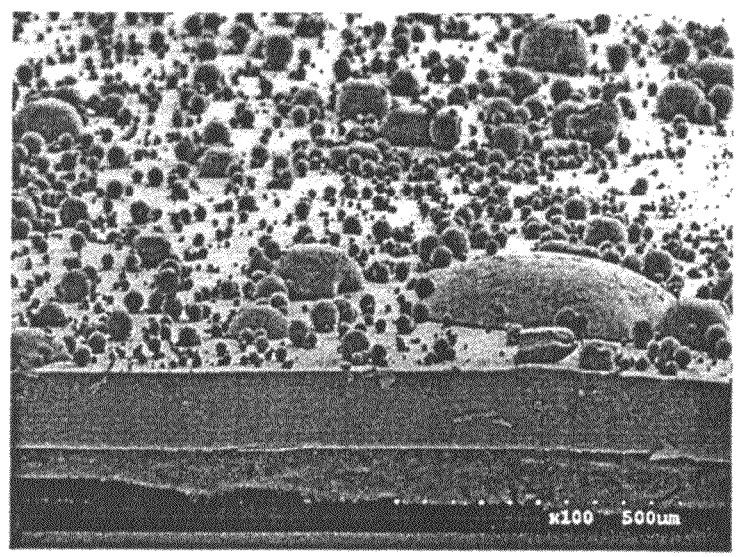
Figure 4C:
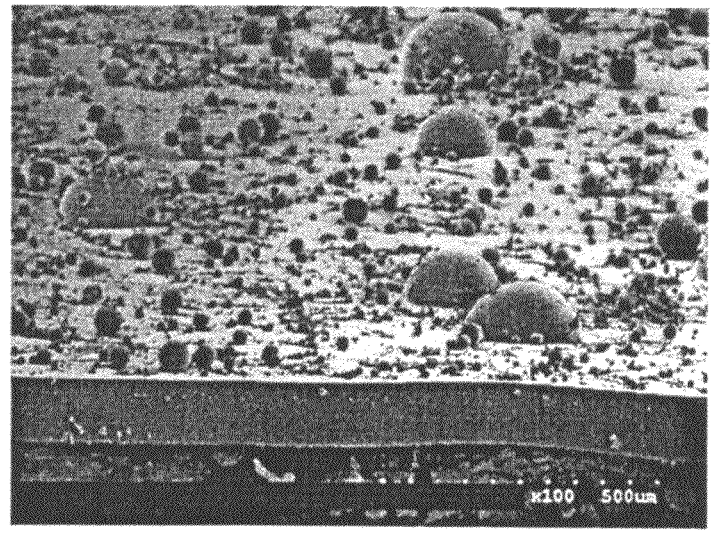
Figure 4D:
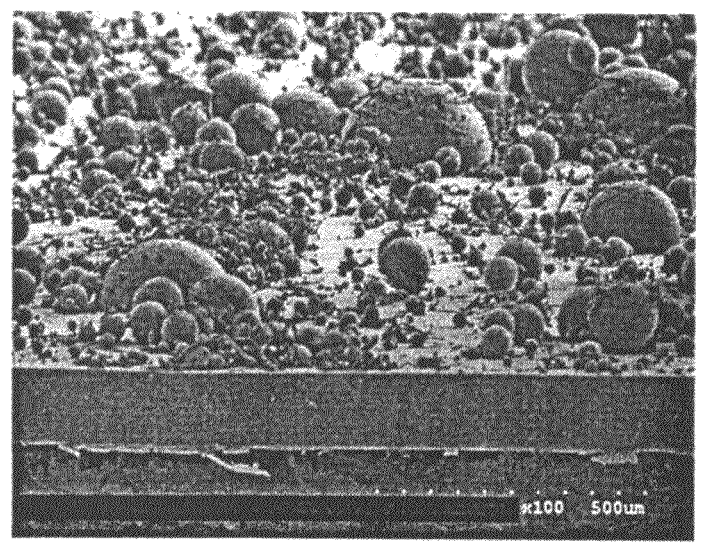

FIGS. 4a-f are images from scanning electron microscope showing exemplary formations on the polymeric film, FIGS. 4a-f were acquired at 100× magnification. Each figure is imprinted with a scale of a series of dots and a value in micrometers. The distance between the dots represents the distance value recited. FIG. 4a is of a phase change solvent on an elastomeric film in a relaxed state; the treated film having been prepared according to the instructions provided below for Example 2. FIG. 4b is the treated film of Example 2 after the film has been stretched to 300% strain and then relaxed. FIG. 4c shows a wax on an elastomeric film in a relaxed state; the treated film having been prepared according to the instructions provide below for Example 1. FIG. 4d is the treated film of Example 1 after the film has been stretched to 300% strain and then relaxed.

Figure 3A:
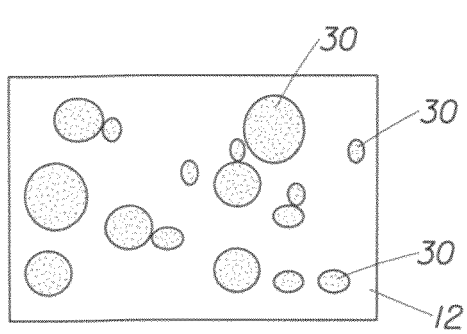
FIGS. 3a-f represent anti-blocking agent formation on a polymeric film.
Figure 3B:
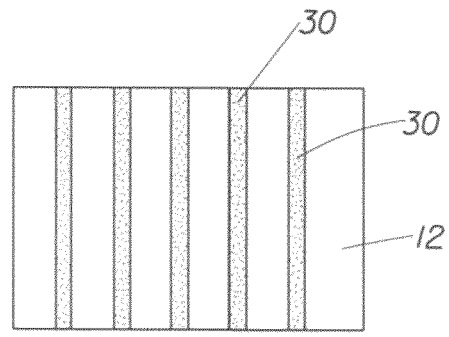
Figure 3C:
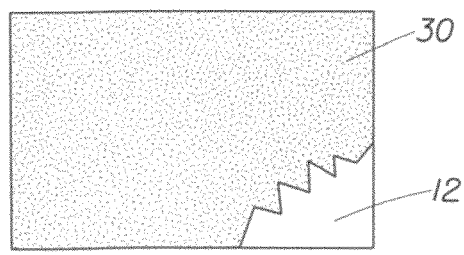
Figure 4E:
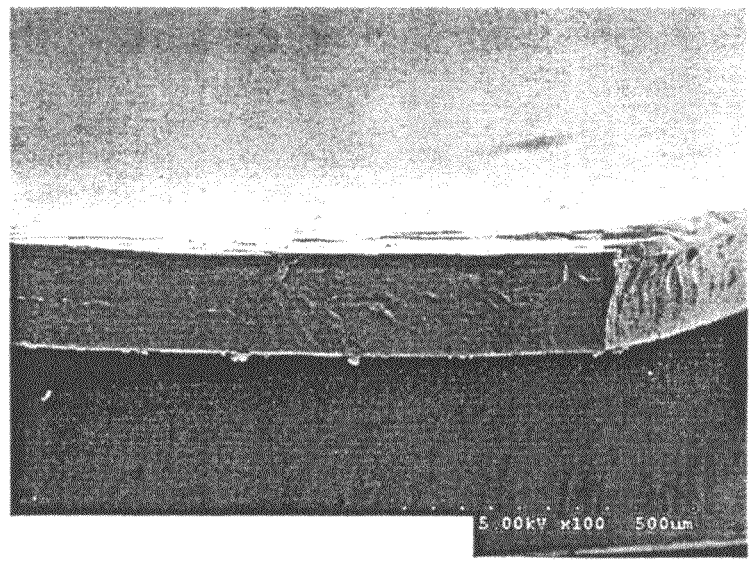

In certain embodiments, the anti-blocking agent 30 may form a coating on the surface of the polymeric film 12, as shown in the cut-away view of FIG. 3c. The coating, may be substantially continuous. FIG. 4e is of a substantially continuous layer of wax on an elastomeric film in a relaxed state; the treated film having been prepared according to the instructions provided below for Example 3. However, in some embodiments the coating may display fissures or cracks in the coating. The coating may maintain a relatively constant thickness over the polymeric film 12. In other embodiments, the coating thickness may vary over the polymeric film and may include areas of no coverage by the anti-blocking agent 30.

Figure 3D:
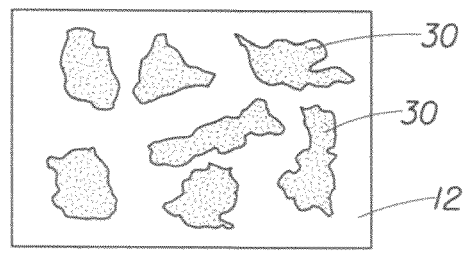
Figure 3E:
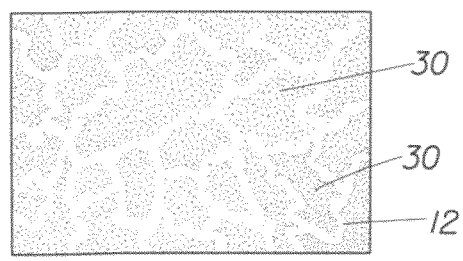
Figure 3F:
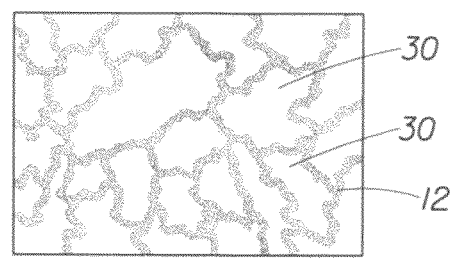
Figure 4F:
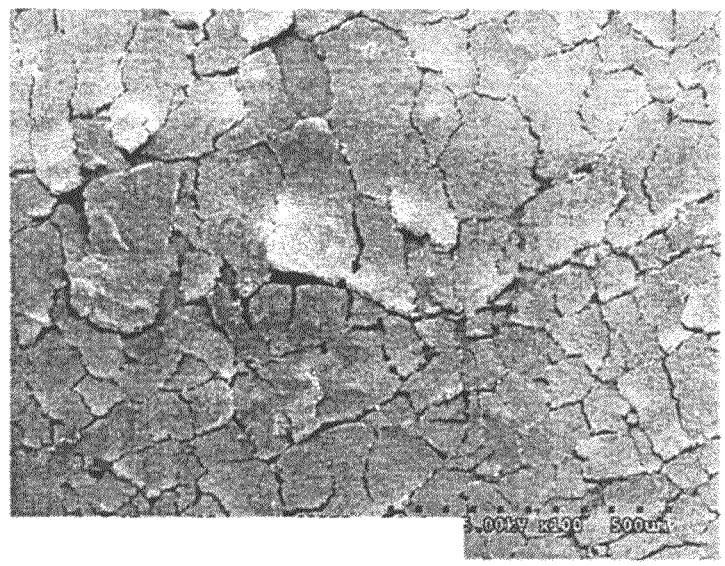

In certain embodiments, the anti-blocking agent 30 forms scales, as shown in FIGS. 3d-e, upon the polymeric film 12. The scales may be substantially discontinuous in that a single scale does not span at least one dimension of the polymeric film 12 surface (i.e., a single scale does span the width and/or the length of the film). In FIG. 3d, the scales of anti-blocking agent 30 may be spaced apart with little to no contact between individual scales. In FIG. 3e, the scales of anti-blocking agent 30 are shown in a more tightly packed configuration where scales may contact one another anal may overlap one another. Scale formation is believed to result from creating a coating of the anti-blocking agent 30 onto the polymeric film 12 and then subjecting the treated film 34 to a strain. It is believed that straining the treated film 34 creates fissures in the coating thereby forming the scales. FIG. 4f shows scale formations of wax on an elastomeric film in a relaxed state. The treated film is prepared according to the instructions provided below for Example 3 and is stretched to 300% strain and then relaxed. As can be appreciated from FIG. 4f, while individual scales are generally planar, scales can bend out of the plane and can overlap other scales.

The anti-blocking agent 30 may comprise any number of commercially available anti-blocking materials. In certain embodiments, the anti-blocking agent 30 substantially comprises an anti-blocking material. The anti-blocking agent 30 may include at least about 30% by weight of anti-blocking material. In other embodiments, the anti blocking agent may include an anti-blocking material in a weight percent of at least about 40%, 50%, 60%, 10%, 80%, 00%, or 95%. It should be recognized that a negligible amount of additives such as stabilizers, colorants, anti-oxidants, and the like may be present in the anti-blocking agent 30. However, such additives are not of a quantity to impact the anti-blocking properties of the agent 30. The anti-blocking material may be a dispersion, solution, or colloidal mixture in a carrier (such as water, aqueous solvents, organic solvents, and the like). In other embodiments, the anti-blocking agent 20 is substantially carrier-free. Suitable anti-blocking materials include phase change solvents; synthetic waxes including homopolymer and copolymer waxes; natural waxes including animal-based, plant-based, mineral-based, and petroleum-based waxes; and combinations thereof.

The anti-blocking agent 30 may comprise one or more phase change solvents. Phase change solvents may be low molecular weight resin or oligomer having one or more low phase change temperatures. Phase change solvents may have at least one phase change temperature in the range from 40° C. to 250° C. Other suitable phase change solvents may have a phase change temperature from 50° C. to 180° C. or, alternatively, from 60° C. to 150° C. The phase change may be a crystalline transition, a glassy transition, a liquid crystalline transition, or combinations thereof. Suitable phase change solvents may have more than one phase change. In certain embodiments, the phase change solvent may represent between about 5% to about 100%, by weight percent, of the anti-blocking agent 30. In other suitable embodiments, the anti-blocking agent 30 consists essentially of one more phase change solvents.

The phase change solvent may have one or more the following structures;

   (I)

   (II)

   (III)

   (IV-a)

   (IV-b)

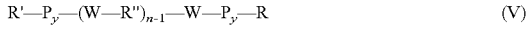   (V)

   (VI)

   (VII)

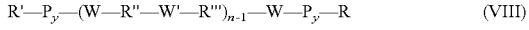   (VIII)

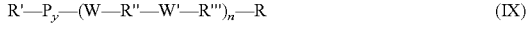   (IX)

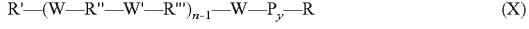   (X)

For formulas (I)-(IV-b), Q is a substituted or substituted difunctional aromatic moiety. Exemplary Q groups are terephthalie, naphthalic, phenolic, phenyl, or biphenyl or mixtures thereof. P may be $CH_2$; R and R' may be the same or different and are independently selected from the group consisting of H, $CH_3$, COOH, $CONHR_1$, $CONR_1R_2$, $NHR_3$, $NR_3R_4$, hydroxy, and C1-C30 alkoxy; wherein $R_1$, $R_2$, $R_3$ and $R_4$ are independently H or linear or branched alkyl from C1-C30; x is an integer from 1 to 30; y is an integer from 1 to 30; and n is an integer from 1 to 7. Q may be substituted on the aromatic ring with one or more substituents selected from the group consisting of H, C1-C30 alkyl, COOH, $CONHR_5$, $CONR_5R_6$, $NHR_7$, $NR_7R_8$, hydroxy, C1-C30 alkoxy, $SO_3H$, and halogen; wherein $R_5$, $R_6$, $R_7$ and $R_8$ are independently H or linear or branched alkyl from C1-C30.

An example of a solvent having formula (III) is:

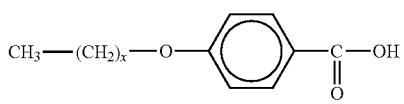

An example of a solvent having formula (I) is as follows:

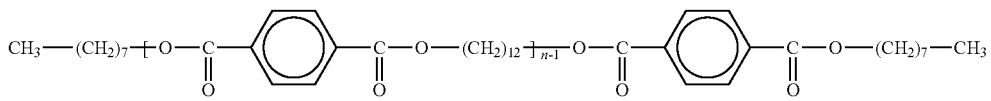

For formulas (V)-(VII), W is selected from the group consisting of —C(=O)—O—, —O—C(=O)—, —I—C(=O)—I—, —C(=O)—NH—, —NH—C(=O)—, imide, —O—, —$NR_9$—C(=O)—O—, and —$NR_9$—C(=O)—$NR_{10}$—, wherein $R_9$ and $R_{10}$ are independently H or linear or branched alkyl from C1-C30; P is $CH_2$; R and R' may be the same or different and are independently selected from the group consisting of H, $CH_3$, COOH, $CONHR_1$, $CONR_1R_2$, $NHR_3$, $NR_3R_4$, hydroxy, and C1-C30 alkoxy; wherein $R_1$, $R_2$, $R_3$ and $R_4$ are independently H or linear or branched alkyl from C1-C30; R" is linear or branched C1-C30 alkyl; y is an integer from 0 to 30, preferably, from 1-30; and n is an integer from 1 to 7. Examples of solvents having formula (V) are as follows;

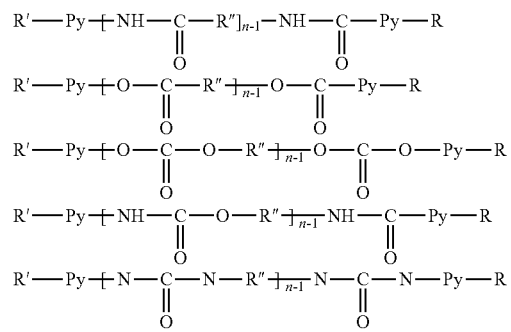

For formulas (VIII)-(X), W and W' am independently selected from the group consisting of —C(=O)—O—, —O—C(=O)—, —O—C(=O)—O—, —C(=O)—NH—, —NH—C(=O)—, imide, —O—, —$NR_9$—C(=O)—O—, —O—C(=O)—$NR_9$—, —$NR_9$—C(=O)—$NR_{10}$—, and —$NR_{10}$—C(=O)—$NR_9$—; wherein when W and W' are the same, R" and R'" are not the same; and wherein $R_9$ and $R_{10}$ are independently H or linear or branched alkyl from C1-C30; P is $CH_2$; R and R' may be the same or different and are independently selected from the group consisting of H, $CH_3$, COOH, $CONHR_1$, $CONR_1R_2$, $NHR_3$, $NR_3R_4$, hydroxy, and C1-C30 alkoxy; wherein $R_1$, $R_2$, $R_3$ and $R_4$ are independently H or linear or branched alkyl from C1-C30; R" and R'" are independently linear or branched C1-C30 alkyl; y is an integer from 0 to 30, preferably, from 1-30; and n is an integer from 1 to 7. A mixture of any of the above solvents having formulas (I)-(X) blended with a thermoplastic polymer is also, contemplated by the present inventors. An example of a solvent having formula (VIII) is as follows where x' an integer from 1 to 30.

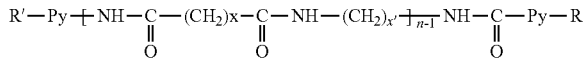

The phase change solvents of the present invention may have a number-average molecular weight from about 150 to about 5000, from about 500 to about 3000, or from about 800 to about 2500. However, higher molecular weight phase change solvents may be used if higher phase change temperatures are required. Additional in relating to phase change solvents is disclosed in U.S. Patent Application Publication No. US2004/0021130A1 entitled "Novel Phase Change Solvents."

The anti-blocking agent 30 may comprise one or more synthetic and/or natural waxes. In certain embodiments, the wax may represent between about 5% to about 100%, by weight percent, of the anti-blocking agent 30. In certain embodiments, the wax represents at least 50%, 60%, 70%, 80%, 90%, or 95% of the anti-blocking agent 30, by weight percent. In other suitable embodiments, the anti-blocking agent consists essentially of one or more waxes.

Suitable synthetic waxes may be derived from a variety of polymers and copolymer waxes. Olefinic polymers and copolymers may be used such as polymethylene wax, polyethylene wax, high density polyethylene wax, polypropylene wax, chemically modified olefinic waxes such as chemically modified polyethylene wax and chemically modified polypropylene wax, copolymer wax, and oxidized olefinic waxes such as oxidized polyethylene wax and oxidized polypropylene wax. Other synthetic waxes may be formed from polyol esters and ethers such as polyethylene glycol and methoxypolyethylene glycol. Other synthetic waxes include oxazoline waxes. Other suitable synthetic waxes include straight chain hydrocarbon waxes such as those formed by the Fischer-Tropsch process.

Suitable natural waxes may include animal-based, plant-based, mineral-based, and petroleum-based waxes. Animal-based waxes may include beeswax, lanolin, spermaceti wax, Chinese insect wax, and shellac. Plant-based waxes include earnauba wax, candelilla wax, Japan wax, ouricury wax, and sugarcane wax. Mineral-based waxes include earth waxed such as ceresin wax, montan wax, and ozokerite. Petroleum-based waxes include microcrystalline wax, paraffin wax, slack, and scale wax.

Suitable waxes for use as the anti-blocking agent 30 may exhibit a Mettler drop point of equal to or greater than 60° C. as measured according to ASTM method D3954. Generally, synthetic waxes may exhibit a density of about 0.85 to about 0.98 g/cm$^3$ as measured according to ASTM method D 1505. Synthetic waxes may exhibit a melt index at 190° C. of from about 1 g to about 5,000 g per 10 minutes as measured by ASTM method D 1238.

Anti-blocking agents 30 suitable for the present invention may have as melting point temperature or soften point temperature of greater than about 30° C. Alternatively, the anti-blocking agents 30 may have a melting point temperature or soften point temperature of greater than about 40° C., 50° C., 60° C., 70° C., 80° C., 90° C. or 100° C.

In certain suitable embodiments, the anti-blocking agent 30 is substantially acrylic free. Substantially acrylic free means that acrylic materials represent no more than 0.05%, by weight percent, of the anti-blocking agent 30. However, in other suitable embodiments, substantially acrylic free means that acrylics represent no more than 0.01% or, alternately, no more than 0.001%, by weight, of the anti-blocking agent 30. In certain embodiments, substantially acrylic free means that the acrylic content is undetectable by conventional quantitative analysis. Acrylics include polymers derived from such compounds as methacrylates, methylmethacrylates, acrylonitriles, ethyl acrylates, N-methylol acrylamides, methacrylamides, melamines, aziridines and the like.

The treated film 34 may be subjected to a step of cooling the treated film, which is shown as item 50 in FIG. 1. As presented above, the anti-blocking agent 30 may be dispensed at an elevated temperature in a molten or softened state and may remain in the molten or softened stated for some period of time after deposit upon the polymeric film 12. In certain embodiments, it is desirable that the anti-blocking agent 30 be cooled prior to gathering the treated film 34. The cooling step 50 may entail use of one or more chilled rolls 52 on which the treated film may be conveyed. Alternatively, the treated film 34 may be passed through a nip point formed by a pair of rollers oriented on parallel axis and positioned to form the nip point. Ideally, the chilled rollers 52 or nip rolls maintain a temperature at or below that of the ambient air or of the polymeric film 12. In another embodiment, the treated film 34 may be passed through one or more blowers passing air over the film. The air may be chilled to expedite the cooling of the molten or softened anti-blocking agent 30. It is also feasible that the cooling step may be a lag time between the steps of applying the anti-blocking agent at station 20 and gathering the treated film at the gathering station 40. Depending upon the anti-blocking agent 30 utilized and the temperature at which the agent is applied, cooling of the deposited anti-blocking agent 30 may be performed at ambient process temperatures (e.g., generally from about 15° C. to about 35° C.) during a lag time. The lag time required to cool and solidify the anti-blocking agent 30 is dependent upon the agent 30 used, the temperature at which the agent 30 is applied, and the ambient process temperature that the treated film 34 encounters. While lag times may be longer, generally it is desirable that the lag time not exceed about 60 seconds so that commercial processing speeds may be maintained.

In certain embodiments, additional process steps may precede the step of gathering the treated film 34 at a gathering station 40. It may be desirable that the treated film 34 be subjected to a consolidation step, designated as item 60 in FIG. 1, where the anti-blocking 30 agent is physically compressed into the polymeric film 12. Consolidation techniques are well known in the art and typically involve as pair of rolls 62, 64 configured to yield a nip point 66 through which the treated film 34 is passed. A consolidated treated film 34 is believed to improve the abrasion resistance of the anti-blocking agent 30 deposited on the polymeric film 12 surface. In other suitable embodiments, the treated film 34 may be subjected to a patterned nip roll. Patterned nip rolls are common in the art for embossing substrates including films, fabric, woven substrate, nonwoven materials, and the like. Other common processing steps may include machine direction elongation, cross-machine direction elongation, or variable direction elongation of the treated film. Apparatus for film elongation are known in the art.

The treated film 34 may be gathered at a gathering station 40. In one embodiment, as shown in FIGS. 1 and 2b, the treated film is conveyed to a bulk roll 42. The bulk roll 42 is typically a substantially cylindrical-shaped roll that rotates about an axis 44. The bulk roll 42 may be rotationally driven by a motor or other known means. The rotation of the bulk roll may impart a tensioning force to the treated film 34. The bulk roll 42 may coil the treated film 34 such that the first surface 14 is in contact with the second surface 16. The bulk roll 42 may gather the film 34 until a suitable size roll is formed. The treated film 34 may experience elevated pressure that may be intensified by the tensioning force applied by the bulk roll 42 or by the resulting size of the bulk roll 42. As the bulk roll 42 gathers the treated film 34 forming successive layers, the outermost layers provide additional weight that may compress the innermost layers of the film 34. Based on the hulk roll 42 tension and size of the gathered bulk roll 42, portions of the treated film 34 may be compressed together at a force of up to about 40 N/cm$^2$. However, in extreme conditions, portions of the treated film 34 may be compressed together at a force of up to about 60 N/cm² and beyond.

The accumulation of the treated film 34 onto the bulk roll 42 may be terminated one the bulk roll 42 reaches a suitable diameter. Generally, the treated film 34 can be severed and the severed edge of the treated film 34 may be rolled onto the bulk roll 42 and secured to prevent unintentional unraveling. The bulk roll 34 may be removed and may undergo additional processing steps.

The treated film 34 may be gathered in other suitable configurations. For example, the treated film 34 may be pleated, folded, or interfolded. In one embodiment, the treated film 34 may be gathered as a stack 46 as is illustrate in the discontinuous process of FIG. 2a. Stacking of the film 34 is often desirable when the film 34 is supplied in a discontinuous manner such as on a piecemeal basis.

The treated film 34 may be subjected to a processing step of being stored in the gathered configuration for some period of time (i.e., a dwell time), which is symbolically represented as item 65 in FIG. 1. The storage step 65 generally extends from the step where the treated film 34 is gathered to a subsequent step where the treated film 34 is removed from the gathered configuration. The storage step 65 may involve the treated film 34 being stored on-site, being stored-off site, and/or being transported. The dwell time of the storage step 65 may be in the order of several minutes or hours. In certain conditions, the dwell time will be for at least 24 hours. In other conditions, the dwell time will be for at least 48 hours. In some instances, the dwell time may encompass a longer period of time on the order of many days or weeks to accommodate for shipping and/or storage of the gathered, treated film 34. In certain circumstances, the treated film 34 may remain in the gathered configuration for a month or longer. Furthermore, the gathered, treated film 34 may be subjected to elevated temperature, which is generally believed to promote blocking in films, during the dwell time. The gathered, treated film 34 may be subjected to a temperature of greater than 30° C. in other embodiments, the gathered, treated film 34 may be subjected to temperatures of greater than 40° C.; alternatively, greater than 50° C.; or alternatively, greater than 60° C.

The gathered, treated film 34 may be subjected to a processing step of being manipulated such that portions of the film 34 in contact are separated from one another. The step, designated as item 70 in FIG. 1, of separating the gathered, treated film 34 is often necessary so that the treated film 34 may be further processed or may be consolidated into another process or integrated into an article such as a diaper. It is not uncommon for the treated film 34 to be gathered at one facility and then transported to another remote facility for separation 70. Separation of the gathered film may be performed by conventional web conveyance mechanisms. For example, for a film 34 on a bulk roll 42, the roll 42 may be spooled or mounted thereby allowing the roll 42 to rotate about its axis 44. The film 34 may be drawn off the roll by application of a linear tension to the film. The tensioning force results in the unspooling of the film 34 from the roll 42. Depending upon the gathering configuration, other mechanisms for film 34 separation may be necessary. For example, in a pleated configuration, the gathered film 34 may be separated by feeding the film through a nip point created by two rollers or onto a roller. For further example, the gathered film 34 may be separated by hand. Regardless of the mechanism chosen, the resulting treated web 34 may be separated such that at least some portions of the treated film 34 that were in contact with one another are detached such that the portions are no longer are in contact.

The treated film 34 should be capable of separation from the gathered state (e.g., a bulk roll 42) with a reasonable amount of force. If excessive force is required to separate the treated film 34 from its gathered state, it suggests that the treated film has blocked. In certain embodiments, the treated film 34 should be separable with an average T-peel force of less than or equal to 20 N/cm. Alternatively, the treated film 34 should be separable with an average T-peel force of less than or equal to 15 N/cm, 10 N/cm, 5 N/cm, or, alternatively, 1 N/cm. All average T-peel force values were determined according to the T-peel force test method disclosed below. While not wishing to be bound by theory, it is believed that resistance to blocking, as evidenced by a low average peel force, is influenced by many factors. For instance, the physical structure of the anti-blocking agent 30 formation can affect blocking. Physical considerations such as the thickness of the formation, the coverage, are of the formation on the film 12, and the number of formation given a specified area may each affect blocking.

The treated film 34, after having been separated from the gathered configuration, may be subjected to further processing. In certain embodiments of the present invention, the treated film 34 may be subjected to a further processing step of lamination, which is designated as item 80 in FIG. 1. The treated film 34 may be joined to a substrate 82 to form a laminate structure 84 by use of bonding rollers 86, 88. In a particular embodiment, the treated film 34 may comprise a polymeric film 12 which may be an elastomeric film. Furthermore, the treated film 34 may be joined to a substrate 82 such as a nonwoven material to form a laminate structure 84 known as a stretch laminate. For example, the treated elastomeric film may be stretched and joined to one or more nonwoven materials while in the stretched configuration. After joining, the film is allowed to relax thereby gathering the nonwoven material(s) and creating, an elastic laminate. In an alternative method, film can be attached to one or more nonwoven materials in a relaxed configuration. The resulting laminate can be made stretchable (or more stretchable in the case of partially stretched strands or film) by subjecting, the laminate to an elongation process which elongates the nonwoven material permanently, but the film is elongated only temporarily. Such processes are known in the art as "zero strain" stretch laminate formation, and the elongation of such laminates may be accomplished with suitable means such as rollers, engaging teeth, or the like. Examples of zero strain activation processing and resulting stretchable laminates are described in U.S. Pat. No. 5,167,897 issued to Weber et al. and U.S. Pat. No. 5,156,793 issued to Buell et at.

In certain embodiments, the treated film 34 may be subjected to a process to impart an elastic-like behavior to the film 34. One suitable method for imparting an elastic-like behavior to the film 34 involves subjecting the film 34 to elongation along, at least on axis of the film 34. This method for imparting an elastic-like behavior to a film is described in U.S. Pat. No. 5,723,087.

Figure 5:
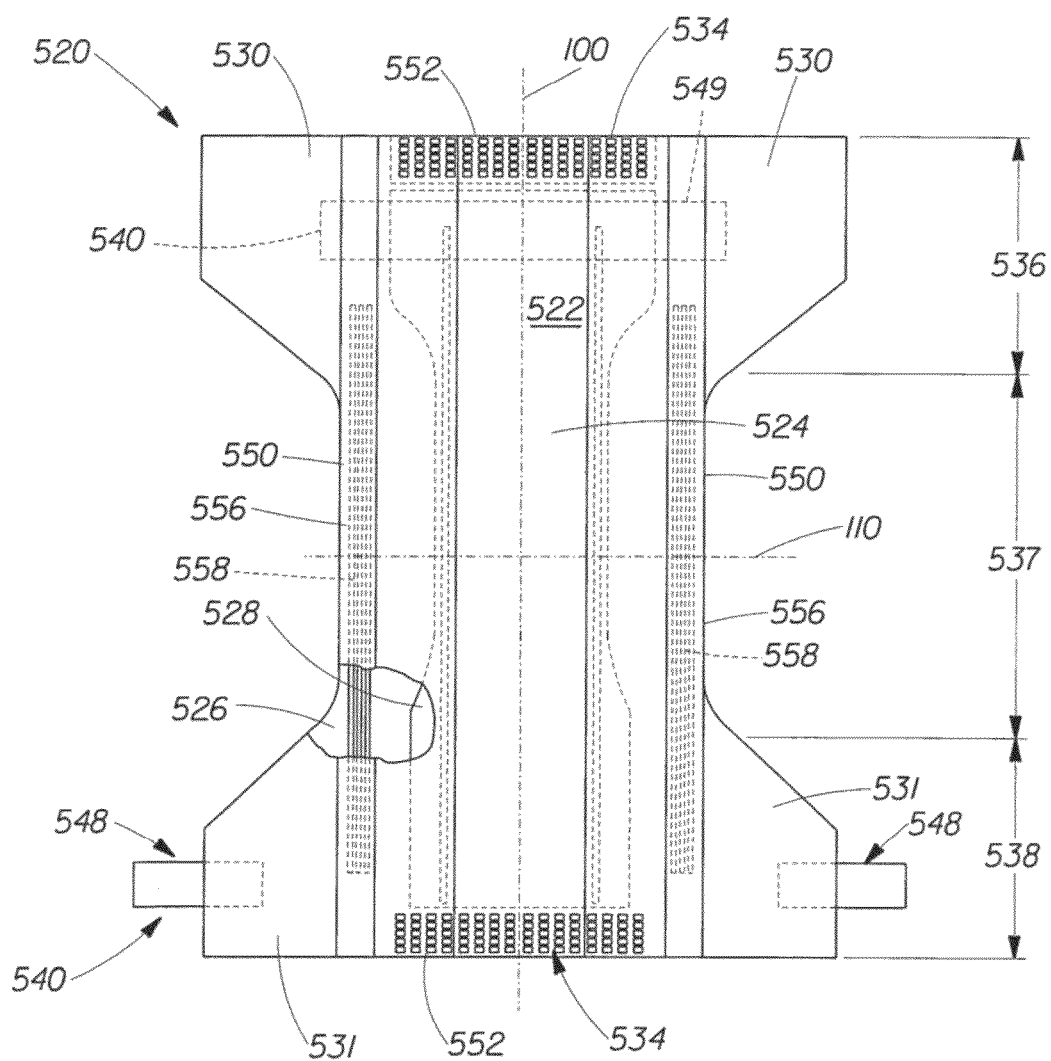
FIG. 5 is a plan view of a diaper in a substantially planar state.

In certain embodiments, the treated film 34 or the laminate structure 84, as disclosed above, may be incorporated into a diaper. FIG. 5 is a plan view of an exemplary diaper 520 in a flat configuration with portions of the structure being cutaway to show underlying elements. The diaper 520 of FIG. 5 exemplifies a traditional open or taped diaper that is manufactured without the waist opening and leg, openings being formed. However, it should be recognized that other diaper configurations are well within the scope of a skilled artisan. Such diaper configurations include pant-type diapers diaper is manufactured with the waist opening and/or the leg openings being formed) and refastenable pant-type diapers.

The portion of the diaper 520 that faces the wearer wearer-facing surface 522) is oriented towards the viewer. The diaper 520 has an opposing garment-facing surface. The diaper 520 may comprise a liquid previous topsheet 524; a backsheet 526; an absorbent core 528 which is preferably positioned between at least a portion of the topsheet 524 and the backsheet 526. The diaper 520 may comprise one or more pairs of side panels, such as a front side panels 530 and rear side panels 531. The diaper may also have elasticized leg cuffs 556, an elasticized waist feature 534, and a fastening system 540. The diaper 520 is shown having a front waist region 536, a rear waist region 538 opposed to the front waist region 536 and a crotch region 537 located between the front waist region 536 and the rear waist region 538. The periphery of the diaper 520 is defined by longitudinal edges 550 run generally parallel to the longitudinal centerline 100 of the diaper 520 and end edges 552 run between the longitudinal edges 550 generally parallel to the lateral centerline 110 of the diaper 520. While the topsheet 524, the backsheet 526, and the absorbent core 528 may be assembled in a variety of well-known configurations such as described generally in U.S. Pat. Nos. 3,860,003; 5,151,092; 5,221,274; 5,554,145; 5,569,234; 5,580411; and 6,004,306. Diaper construction as well as topsheet, backsheet, and absorbent core production are well known in the art.

The absorbent core 528 may comprise a wide variety of liquid-absorbent materials commonly used in disposable diapers and other absorbent articles such as comminuted wood pulp; creped cellulose wadding; melt blown polymers, including co-form; chemically stiffened, modified or cross-cellulosic fibers; tissue, including tissue wraps and tissue laminates; absorbent foams; absorbent sponges; superabsorbent polymers; absorbent gelling materials; superabsorbent fibers; or any other known absorbent material or combinations of materials.

The backsheet 526 may be substantially impervious to liquids (e.g., urine) and may comprises a laminate of a nonwoven and a thin plastic film such as a thermoplastic film having a thickness of about 0.012 mm (0.5 mil) to about 0.051 mm (2.0 mils). A suitable backsheet may comprise the treated film as described above or a laminate comprising the treated film. Other suitable bark beet films include those manufactured by Tredegar Industries Inc. of Terre Haute, Ind. and sold under the trade names X15306, X10962, and X10964. Other suitable backsheet materials may include breathable materials that permit vapors to escape from the diaper 20 while still preventing exudates from passing through the backsheet 526. Exemplary breathable materials may include materials such as woven webs, nonwoven webs, composite materials such as film-coated nonwoven webs, and microporous films. Suitable microporous films are manufactured by Mitsui Chemicals, Inc., of Japan under the designation ESPOIR and by Tredegar Industries under the designation EXAIRE, Suitable breathable composite materials comprising polymer blends are available from Clopay Corporation, Cincinnati, Ohio under the name HYTREL blend P18-3097. Other breathable baeksheets including nonwoven webs and apertured formed films are described in U.S. Pat. No. 5,571,096.

The topsheet 524 may be compliant, soft feeling, and non-irritating to the user's skin. The topsheet 524 is generally liquid previous permitting liquids (e.g., urine) to readily penetrate through its thickness. A suitable topsheet may be manufactured front a wide range of materials, such as porous foams, reticulated foams, apertured plastic films, aperture non-woven webs, or woven or non-woven webs of natural fibers (e.g., wood or cotton fibers), synthetic fibers (e.g., polyester or polypropylene fibers), or a combination of natural and synthetic fibers. Preferably, the topsheet 524 may be made of a hydrophobic material to isolate the user's skin from liquids contained in the absorbent core 528 (i.e., prevent "rewet"), unless the article is intended to provide at least a partial wetness sensation to the user, as is desirable in certain training pant articles.

The front and rear side panels 530, 531 may be disposed in the respective front and rear waist regions 536, 538 of the diaper 520. For a diaper that is provided in an open configuration (i.e., the diaper has a fastening system 540 that is manufactured in an unfastened configuration), the front and rear side panels 530, 531 may be joined by way of the fastening system 540 upon application of the diaper so as to form a waist opening and a pair of leg openings. For pant-type diapers, the front and rear side panels 530, 531 may be pre-joined during manufacture so as to form a waist opening and a pair of leg openings. The front and rear side panels 530 and 531 may be elastic or extensible to provide a more comfortable and contouring fit by initially conformably fitting the diaper 520 to the wearer. The side panels 530, 531 may sustain this fit throughout the time of wear including, when the diaper 520 has been loaded with exudates since the elasticized site panels 530, 531 allow the sides of the diaper 520 to expand and contract. The side panels 530, 531 may comprise an elastomeric film or a stretch laminate. The side panels 530, 531 may comprise a treated film as described above or a laminate comprising the treated film, it is generally desirable that the treated film be elastic.

The diaper 520 may also comprise at least one waist feature 534 that helps to provide improved fit and containment. The waist feature 534 may be elastic and/or extensible. The waist feature 534 may comprise a treated film as described above or a laminate comprising the treated film. It may be desirable that the treated film be elastic. Exemplary waist feature constructions include those described in U.S. Pat. No. 4,515,595 and U.S. Pat. No. 5,221,274.

The diaper 520 may also include one or more elasticized leg cuffs 556 to provide better fit, containment, and aesthetic characteristics. Leg cuffs are known variously in the art as gasketing cuffs, containment flaps, "stand-up" elasticized flaps, barrier cuffs, leg bands, side flaps, and/or elastic cuffs. The elasticized leg cuff 556 may comprise one or more elastic members 558 that can impart elasticity to the cuff 556. The elasticized cuff 556 may comprise a treated film as described above or a laminate comprising the treated film. It may be desirable that the treated film be elastic so as to be used as the elastic member 558. Leg cuffs 556 may be constructed in any suitable configuration known in the art, including those described in U.S. Pat. No. 4,695,278 and U.S. Pat. No. 4,795, 454.

The diaper 520 may include a fastening system 540 that, when fastened, joins the front waist region 536 and the rear waist region 538 to form a waist opening. The fastening system 540 may comprise a fastener 548 and a receiving member 549 such as tape tabs and landing zone, hook and loop fastening components, interlocking fasteners such as tabs & slots, buckles, buttons, snaps, and/or hermaphroditic fastening components, although any other known fastening means are generally acceptable. Some exemplary surface fastening systems are disclosed in U.S. Pat. Nos. 3,848,594; 4,894,060, 4,946,527; 6,431,098; 4,699,622; and 5,242,436.

T-Peel Test Methods

This T-peel method is used to quantify the amount of force required to separate the treated film from itself after some prescribed dwell time.

Sample Preparation—

Figures 6A, 6B:
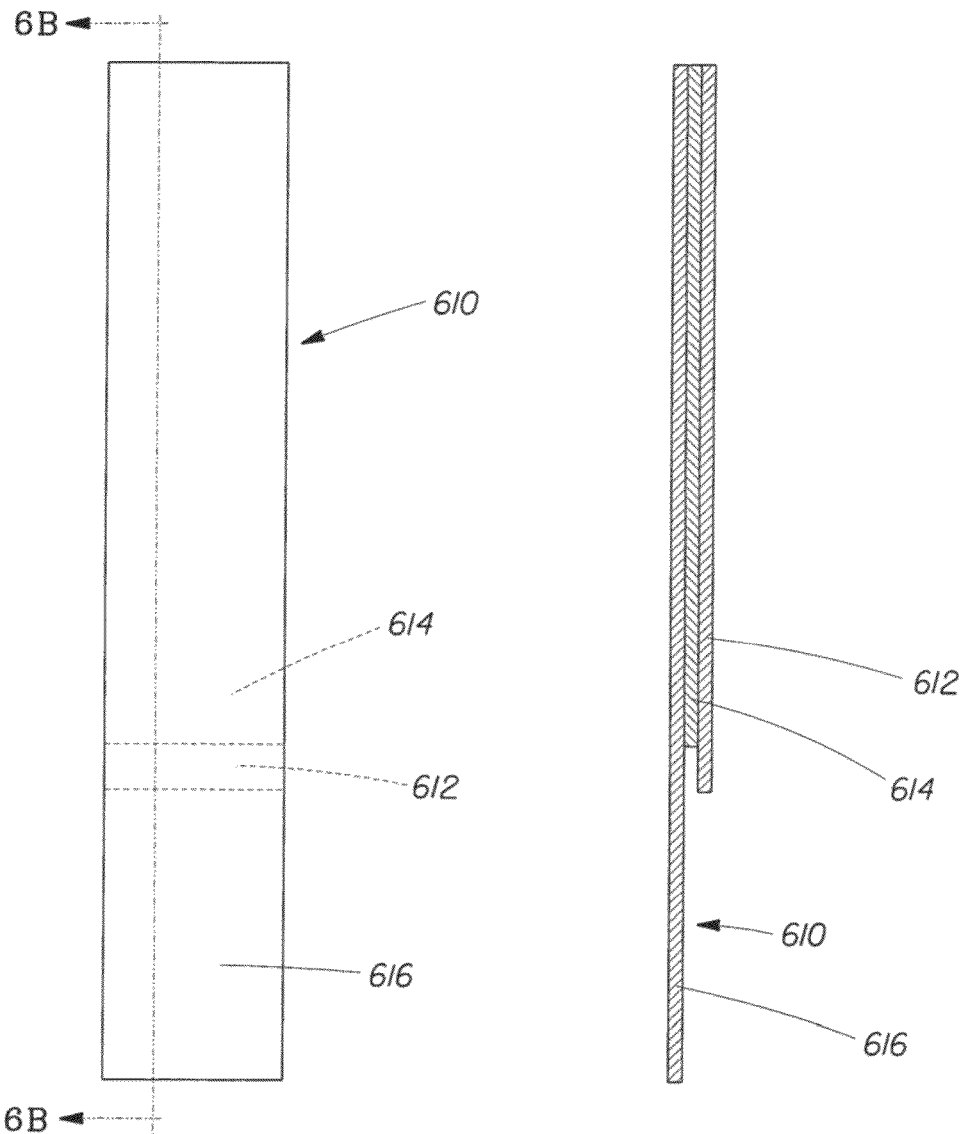
FIGS. 6a-c are drawings of a sample formation for a T-Peel Test.

The samples are prepared as a three layer laminate of treated film, double sided tape, and poly(ethylene terephthalate) (PET) film. The resulting sample 610 is a three layer laminate as depicted in planar view in FIG. 6a. FIG. 6b shows a cross-section view, as taken along sectional line b-b of FIG. 6a, of the three layer laminate. The PET film, designated item 616, is 2 mil (0.05 mm) thick. It is rectangular in shape and has the dimensions of about 54 cm (1.0 inch) wide and about 15.24 cm (6 inches) long. The PET is used to prevent stretching of the treated film during the T-peel test. Any commercially available PET film having or resized to have the recited dimensions may be used.

A rectangular piece of double sided tape, designated item 614, having the dimensions of about 2.54 cm (1 inch) by about 10.16 cm (4 inch) is bonded to PET film. A suitable double sided tape is a double sided tape available from Avery Denninson Corp., Painesville, Ohio, under the supplier code of Fr 239. The double sided tape is positioned so that three edges are coterminous with the edges of the PET film.

A rectangular piece of the treated film, designated item 612, (i.e., film being subjected to T-peel test) having the dimensions of about 2.54 cm (1 inch) by about 10.795 cm (4.25 inches) is bonded to the double sided tape. The treated film is positioned so that three edges are coterminous with the edges of the PET/double sided tape laminate. Care is required in handling the treated film 612 to avoid contamination of the treated film 612.

A piece of protective paper is placed over the treated surface of the treated film/double-sided tape/PET laminate. The laminate is rolled with a 4.5 pound (2 kg) HR-100 ASTM 80 shore rubber-faced roller. Ten full strokes are applied to the sample at a speed of approximately 100 mm/sec along the length of the laminate.

Figure 6C:
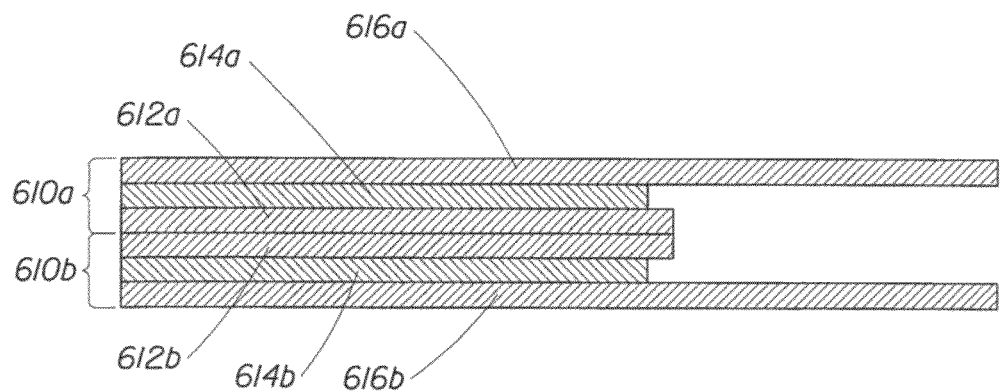

The protective paper is removed from the treated film double-sided tape/PET laminate and pairs of treated film/double-sided tape/PET laminate are placed onto each other such that the treated surfaces are engaged in a face-to-face relationship to define a bonded area. FIG. 6c is a side view showing a pair of laminates in such a face-to-face relationship. A first laminate, designated as item 610a, comprises a PET film 616a, a double sided tape 614a, and a treated film 612a. A second laminate, designated 610b, comprises a PET film 616b, a double sided tape 614b, and a treated film 612b. The first laminate 610a is joined to the second laminate 610b such that the surface of treated film 612a is in contact with the surface of treated film 612b. Both film 612a and 612b should be substantially coterminous with a bonded area having the dimensions of approximately 2.54 cm (1 inch) wide by 10.795 cm (4.25 inches) long. The bonded pair sample is aged at a temperature of 60° C. and under a pressure of 414 kPa (60 psi) for a minimum of 12 hours but no more than 24 hours prior to testing.

A skilled artisan should recognize that the three layer laminate may be formed from components having larger dimensions than those described above. The individual components may be resized from the larger dimension and then laminated together or may be laminated together and resized. Furthermore, while the dimensions provided above are preferred for testing and should be followed, a skilled artisan should recognize that bonded specimens of other dimensions may be used in the T-Peel Method. The resultant T-Peel force is normalized by dividing force by the bonded width in centimeters (i.e., "bonded width" being the width of the bonded area measured substantially parallel to the grip width once the sample is mounted in the tensile tester).

Test Conditions—

The T-peel test method is performed in a controlled condition room at 23° C.+/−5° C. A suitable instrument for this test is a tensile tester commercially available as Instron 5564 from Iristron® Engineering Corp., Canton, Mass. The instrument is interfaced with a computer loaded with the Instron® Merlinmi Material Testing Software which controls the testing parameters, performs data acquisition and calculation, and provides graphs and data reports. Typically, 1 inch (2.54 cm) wide grips are used. The grips are air-actuated and designed to concentrate the entire gripping force along a plane perpendicular to the direction of testing stress. A load cell is selected so that the forces measured will not exceed 90% of the capacity of the load cell or the load range used e.g., typically, as a 10N, 50N or 100N load cell). The instrument is calibrated according to the manufacturer's instructions. The distance between the lines of the gripping force (i.e., gauge length) is set to 1" (2.54 cm).

Figure 6D:
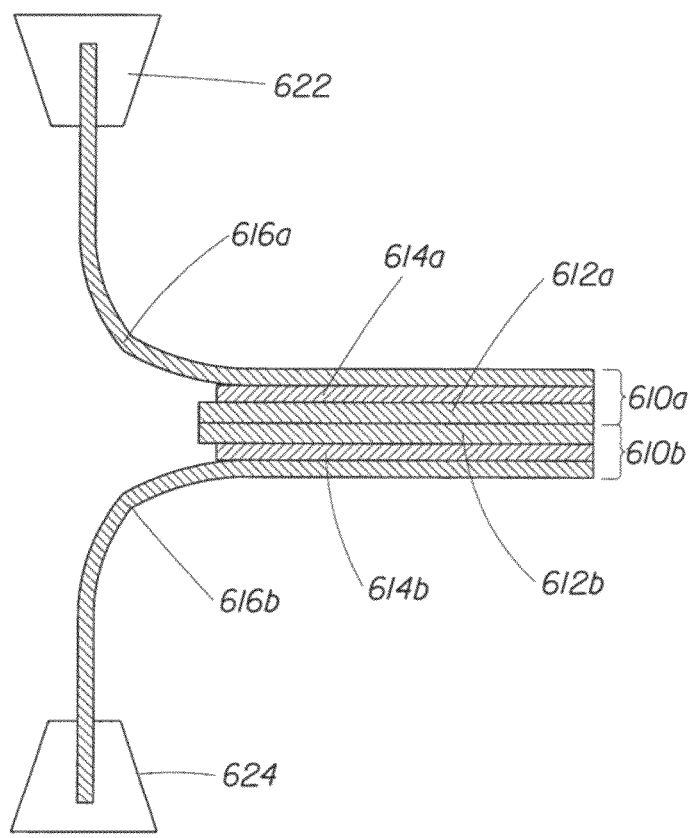
FIG. 6d shows a sample such as the one of FIG. 6c mounted on the clamps of a tensile tester.

The bonded pair of laminates 610a and 610b, as prepared according the Sample Preparation as described above and shown in FIG. 6c, is mounted into the grips 622, 624 as shown in FIG. 6d. The free end (i.e., end furthest from the bonding area) of one of the PET films 616a is mounted into top, movable grip 622, and the free end of the other PET film 616b is mounted into the bottom, stationary grip 624. The PET film 616a is bonded to double sided tape 614a and treated film 612a. The PET film 616b is bonded to double sided tape 614b and treated film 616b. The sample is mounted into the grips in a manner such that there is no slack in the laminates 610a and 610b between the grips, as shown in FIG. 6d. The load reading on the instrument is zeroed.

Once mounted in the grips, the grips are separated using a crosshead speed of 12 inches/min (305 mm/min). The gauge length is increased until the treated films 612a and 612b are separated from each other or the sample fails (i.e., laminate tears or the sample delaminates at an interface other than between the two treated films 612a and 612b). A peak load is recorded. An average load is calculated from the loads recorded between 1 inch and 3.5 inches of the crosshead extension. (If the sample length is not 4 inches, the average load is calculated from the loads recorded crosshead extension between 25% to 87.5% of the sample length. For example, if the sample is 6 inches long, the average load is calculated between 1.5 inches and 5.24 inches of crosshead extension.) The average load is normalized and reported in units of N/cm: normalized load=average load÷initial bond width in centimeters. The peak load is also normalized in the same fashion and reported in N/cm.

As recited in the definitions above, a sample is considered "blocked" if de-lamination, occurs between an interface (e.g., between 616a and 614a, 614a and 612a, 612b and 614b, car 614b and 616b in FIG. 6d) other than the interface between the two treated films (items 612a and 612b in FIG. 6d). If a specimen is "blocked" no values are reported for the peak and average forces. A sample is considered "non-blocked" if the treated films 612a and 612b fully separate from each other with no de-lamination between 616a and 614a, 614a and 612a, 612b and 614b, or 614b and 616b.

EXAMPLES

Example 1

8 gsm Polyethylene Wax on an Elastomeric Film

Film: A 12.7 cm (5.0 inch) wide by 55.88 cm (22 inch) cast extruded film (0.120 mm thick) is formed with a composition of about 79.5 weight percent (%) Vector 4211 (a SIS block copolymer available from Dexco Chemical Company, Houston, Tex.), about 11% Drakeol 600 mineral (available from Penreco Company, Dickenson, Tex.), about 9 weight NVA3900 Polystyrene (available from Nova Chemical Corporation, Calgary, Alberta, Canada), about 0.25 weight % Iizanox 1010 (available from Ciba Chemicals, Tarrytown, N.Y.), and about 0.25 weight % Ergafos 168 (available from Ciba Chemicals, Tarrytown, N.Y.).

Anti-Blocking Agent: The anti-blocking agent consists essentially of a polyethylene wax such as A-C 617 available from the Honeywell Corporation, Morristown, N.J.

Application: The film is spray coated using a PAM 600 sprayer (available from PAM Fastening Technology, Charlotte, N.C.). The sprayer is heated to approximately 260° F. The anti-blocking agent is atomized and propelled using a stream of 60 psi compressed air. The anti-blocking agent is sprayed with the sprayer held 17.78 cm (7 inches) above the surface of the film supported on table. Approximately 0.5402 grams of anti-blocking agent is evenly applied so as to result in a normalized coating basis weight of 8 g/m$^2$.

Example 2

8 gsm Phase-Change Solvent on an Elastomeric Film

Film: Same as described in Example 1.
Anti-Blocking Agent: The anti-blocking agent consists essentially of a phase change solvent, alpha-octyl-omega-octyl-oligo(dodecyl terephthalate), with the following structure is used:

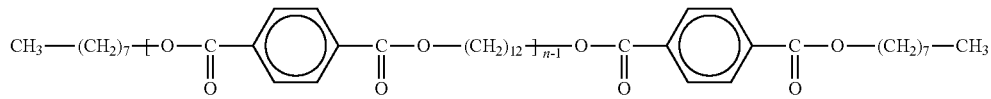

In the above structure, the value of n−1 averages about 1.8-2.1.

Application: The film is spray coated using a PAM 600 sprayer (available from PAM Fastening Technology, Charlotte, N.C.). The sprayer is heated to approximately 260° F. The anti blocking agent is atomized and propelled using a stream of 60 psi compressed air. The anti-blocking agent is sprayed with the sprayer held 17.78 cm (7 inches) above the surface of the film supported on table. Approximately 0.5402 grams of anti-blocking agent is evenly applied so as to result in a normalized coating basis weight of 8 g/m$^2$.

Example 3

10.6 gsm Polyethylene Wax on an Elastomeric Film

Film: Same as described in Example 1.
Anti-Blocking Agent: Same as described in Example 1.
Application: The film is spray coated using a PAM 600 sprayer (available from PAM Fastening Technology, Charlotte, N.C.). The sprayer is heated to approximately 260° F. The anti-blocking agent is atomized and propelled using a stream of 35 psi compressed air, The anti-blocking agent is sprayed with the sprayer held 5.08 cm (2 inches) above the surface of the film supported on table. Approximately 0.24 grams of anti-blocking agent is evenly applied so as to result in a normalized coating basis weight of 10.6 g/m$^2$. The anti-blocking agent is further melted by pressing the spray coated film in a heated hydraulic press as is available from Carver Inc., Wabash, Ind. The press is heated to 280° F. and the film may be pressed under a load of 2,000 pounds for 1 second. The anti-blocking agent forms a semi-continuous layer.

Example 4

4.9 gsm Polyethylene Wax on an Elastomeric Film

Film: Same as described in Example 1.
Anti-Blocking Agent: Same as described in Example 1.
Application: Same application technique as described in Example 3 but with following modifications. Approximately 0.11 grams of anti-blocking agent is evenly applied so as to result in a normalized coating basis weight of 4.9 g/m$^2$.

Comparative Example 5

Neat Elastomeric Film

Film: The film as described in Example 1 is used.
Anti-Blocking Agent: None.
Test Results
Examples 1-5 are to be aged at 60° C. and 414 kPa (60 psi for 17 hours prior to testing. Examples 1-5 are then subjected to the test conditions as described above. Table 1 summarizes the results of the T-Peel Test for each of the Examples. The Examples having the anti-blocking agent exhibit a resistance to blocking. The peak and average loads for Examples 1-4 are within a feasible processing range. Example 5 shows blocking. Example 5 delaminated at the film-adhesive tape interface. The films were blocked and unable to be peeled apart. As can be appreciated from the test results, the treated films exhibit a significant reduction of blocking compared to the untreated film.

TABLE 1

| Sample | Peak Load, N/cm | Average Load, N/cm |
|---|---|---|
| Example 1* | 7 | 4 |
| Example 2** | 13 | 5 |
| Example 3*** | 0.3 | 0.1 |
| Example 4*** | 0.2 | 0.1 |
| Example 5**** | — | — |

*Average of four specimens
**Average of three specimens
***Average of two specimens
****Two specimens were completely adhered to one another; the bond between test film and adhesive failed.

All documents cited in the Detailed Description of the Invention are, in relevant part, incorporated herein by reference; the citation of any document is not to be construed as an admission that it is prior art with respect to the present invention. To the extent that any definition or meaning of a term in this written document conflicts with any definition or meaning of the term in a document incorporated by reference, the definition or meaning assigned to the term in this document shall govern.

While particular embodiments of the present invention have been illustrated and described, it would be obvious to those skilled in the an that various other changes and modifications can be made without departing from the spirit and scope of the invention, it is therefore intended to cover in the appended claims all such changes and modifications that are within the scope of this invention.

What is claimed is:

1. A method of forming a roll of thermoplastic elastomeric film resistant to blocking, and using said film, said method comprising the steps of:
   a) providing a thermoplastic elastomeric film having a first surface and a second surface in a continuous manner by on-line formation by extrusion,
   b) following formation of the film by extrusion, applying an anti-blocking agent in a molten state to at least the first surface of the film to form a discontinuous formation of said anti-blocking agent on said first surface, and thereby form a treated surface, and
   c) following formation of said treated surface, gathering the film on a roll to form a bulk roll having rolled layers of the film with the treated surface in contact with the second surface.

2. The method of claim 1 wherein the film comprises a polymer selected from the group consisting of polyvinylarenes, styrenic block copolymers, polyolefins, metallocene-catalyzed polyolefins, polyesters, polyurethanes, polyether amides, and combinations thereof.

3. The method of claim 1 wherein the anti-blocking agent comprises a material selected from the group consisting of a phase change solvent, a wax, and combinations thereof.

4. The method of claim 1 wherein the anti-blocking agent comprises a wax selected from the group consisting of animal-based waxes, vegetable-based waxes, petroleum-based waxes, synthetic waxes, mineral-based waxes, and combinations thereof.

5. The method of claim 1 wherein the anti-blocking agent comprises a wax which exhibits a property selected from the group consisting of:
   a) a Mettler drop point equal to or greater than about 60° C.,
   b) a density from about 0.85 to about 0.98 g/cm$^3$,
   c) a melt index at 190° C. from about 1 g to about 5,000 g per 10 minutes, and
   d) combinations thereof.

6. The method of claim 1 wherein the step of applying the anti-blocking agent in a molten state further comprises applying the anti-blocking agent as a fine mist; said fine mist having an average particle diameter of less than or equal to 1000 μm.

7. The method of claim 1 further comprising the step of cooling the treated film; wherein the step of cooling is performed prior to the step of gathering the treated film.

8. The method of claim 1 further comprising the step of consolidating the treated film wherein the anti-blocking agent and polymeric film are compressed together; wherein the step of consolidating is performed prior to the step of gathering the treated film.

9. The method of claim 1 further comprising the step of storing the gathered film for a dwell time of at least about 24 hours.

10. The method of claim 1 further comprising the step of separating the gathered film, said separation results in the detachment of at least some portion of the gathered film that was in contact with itself and wherein the separation requires an average T-Peel force of less than or equal to about 20 N/cm.

* * * * *